(12) United States Patent
Miller et al.

(10) Patent No.: US 6,586,479 B2
(45) Date of Patent: Jul. 1, 2003

(54) PROCESS FOR PREPARING FINE EMULSIONS

(75) Inventors: Dennis Miller, Kelkheim (DE); Torsten Henning, Kelkheim (DE); Wiebke Johannpeter, Steinbach (DE); Eva-Maria Wiener, Hofheim-Diedenbergen (DE)

(73) Assignee: Clariant GmbH, Frankfurt (DE)

( * ) Notice: Subject to any disclaimer, the term of this patent is extended or adjusted under 35 U.S.C. 154(b) by 5 days.

(21) Appl. No.: 09/910,541

(22) Filed: Jul. 20, 2001

(65) Prior Publication Data
US 2002/0072544 A1 Jun. 13, 2002

(30) Foreign Application Priority Data
Jul. 21, 2000 (DE) .......................................... 100 35 930

(51) Int. Cl.⁷ ............................ B01F 17/30; B01F 17/34
(52) U.S. Cl. .................. 516/73; 424/70.19; 424/70.21; 516/27; 516/28; 516/29; 516/70; 516/925
(58) Field of Search .............................. 516/27, 28, 70, 516/73, 925, 29; 424/70.19, 70.21

(56) References Cited

U.S. PATENT DOCUMENTS

| | | | | |
|---|---|---|---|---|
| 2,294,140 A | * | 8/1942 | Taylor ....................... | 516/73 X |
| 2,347,178 A | * | 4/1944 | Fritz et al. .................... | 516/27 |
| 3,705,855 A | * | 12/1972 | Marschner ................. | 516/73 X |
| 3,829,563 A | * | 8/1974 | Barry et al. | |
| 5,206,316 A | * | 4/1993 | Chuang ....................... | 516/27 |
| 5,244,598 A | * | 9/1993 | Merrifield et al. | |
| 5,298,240 A | | 3/1994 | Schroder et al. ......... | 424/401 X |
| 5,759,558 A | * | 6/1998 | Epstein et al. ............. | 516/27 X |
| 5,858,334 A | * | 1/1999 | Ascione et al. .......... | 424/401 X |
| 5,972,361 A | * | 10/1999 | Fowler et al. ........ | 424/70.19 X |
| 6,350,783 B2 | * | 2/2002 | Honda et al. ......... | 424/70.19 X |

FOREIGN PATENT DOCUMENTS

| | | |
|---|---|---|
| DE | 195 09 079 | 9/1996 |
| DE | 196 42 090 | 4/1998 |
| EP | 0 490 053 | 6/1992 |
| EP | 0 669 125 | 8/1995 |
| EP | 1 029 586 | 8/2000 |

OTHER PUBLICATIONS

EPO Search Report for EP Application No. 011116912, mail date Sep. 24, 2001.
English abstract for DE 195 09 079, Sep. 19, 1996.
English abstract for DE 196 42 090, Apr. 9, 1998.
U.S. patent application Ser. No. 09/505,293.

* cited by examiner

Primary Examiner—Richard D. Lovering

(57) ABSTRACT

The invention relates to fine emulsions comprising at least one W/O emulsifier and at least one hydrophilic component, and to a process for their preparation. The fine emulsions are obtainable by converting a W/O preemulsion comprising at least one W/O emulsifier into an O/W fine emulsion by adding at least one hydrophilic component and, where appropriate, changing the temperature. Suitable W/O emulsifiers are preferably sorbitol esters. The fine emulsions are preferably spray emulsions for cosmetic and pharmaceutical applications.

8 Claims, No Drawings

PROCESS FOR PREPARING FINE EMULSIONS

BACKGROUND OF THE INVENTION

The invention relates to fine emulsions comprising sorbitol esters, and to a process for the preparation of such fine emulsions.

DESCRIPTION OF THE RELATED ART

Fine emulsions or microemulsions are low-viscosity, optically transparent dispersions of two immiscible liquids which are stabilized by at least one ionic or nonionic surfactant. In the case of fine emulsions, the particle diameters are in the range from about 0.1 to 10 micrometers. The interfacial tension between the two phases is extremely low.

The viscosity of many fine emulsions of the O/W type is comparable with that of water.

In contrast to fine emulsions, "macroemulsions" have high viscosities and their particle diameter is in the range from about 10 to 100 micrometers. Macroemulsions are milky white in color and, upon heating, tend toward phase separation or toward sedimentation of the dispersed substances.

Sprayable emulsions call for low viscosities (about 100 mPas), as are realizable in the case of fine emulsions even at room temperature.

With regard to cosmetic and pharmaceutical applications, spray emulsions have decisive advantages over the classic emulsions formulated as lotions, creams or ointments. For example, spray emulsions impart a pleasant feel to the skin, can be readily dosed and are protected against contamination.

According to the prior art, fine emulsions can be prepared by the "hot/hot process". In the "hot/hot process", the fatty phase is heated to about 75° C., melted completely and combined with the water phase, likewise at about 75° C., using an extremely high input of mechanical energy in order to ensure rapid dispersion and to achieve high fineness of the system. This process requires high thermal and mechanical energy expenditure.

A second process, the "phase inversion temperature (PIT) process" makes it possible to dispense with intensive mechanical dispersion operations. The "phase inversion temperature process" is based on the fact that the O/W character of a hydrophilic, nonionic surfactant decreases with increasing temperature and converts to the W/O type at a certain conversion temperature. Upon cooling, conversion back to the O/W type takes place. The conversion temperature is referred to as the "phase inversion temperature (PIT)". In the preparation of the emulsion, the procedure involves dissolving the actually hydrophilic emulsifier above its PIT in a preferably polar oil phase and emulsifying it with the water phase. Upon cooling, a transparent microemulsion is firstly traversed, then highly disperse, low-viscosity formulations form without a homogenization step.

A disadvantage of the PIT process is that it is limited to ethoxylated surfactants which display a sufficiently high temperature dependency of their hydrophilic/lipophilic properties.

The use of ethoxylated surfactants for cosmetic and pharmaceutical uses is, however, problematic since they are suspected of making the skin permeable to harmful substances and of forming undefined, possibly harmful substances under the action of UV.

Accordingly, it was an object of the invention to develop fine emulsions which can be prepared without the use of ethoxylated products and without high thermal and/or mechanical energy expenditure.

SUMMARY OF THE INVENTION

Surprisingly, it has been found that fine emulsions comprising at least one W/O emulsifier and at least one hydrophilic component can be prepared without the use of ethoxylated products and without high thermal and/or mechanical energy expenditure.

DESCRIPTION OF THE PREFERRED EMBODIMENTS

The invention thus provides fine emulsions comprising at least one W/O emulsifier and at least one hydrophilic component.

The particle size of the fine emulsions according to the invention is preferably in the range from 0.1 to 10 micrometers.

The fine emulsions preferably comprise 0.01 to 10% by weight, particularly preferably 0.1 to 8% by weight and especially preferably 0.2 to 4% by weight, of W/O emulsifiers.

The fine emulsions preferably comprise 0.01 to 10% by weight, particularly preferably 0.1 to 7% by weight and especially preferably 0.3 to 5% by weight, of hydrophilic components.

The nonaqueous fraction of the fine emulsions, which is largely composed of the W/O emulsifiers and the oily substance, is preferably 0.1 to 95% by weight and particularly preferably 0.5 to 45% by weight.

The fine emulsions are preferably those obtainable by converting a W/O preemulsion comprising at least one W/O emulsifier into an O/W fine emulsion by adding at least one hydrophilic component and, where appropriate, changing the temperature.

The conversion of the W/O preemulsion into the O/W fine emulsion preferably takes place without increasing the temperature.

As W/O emulsifiers, preference is given to using sorbitol esters, polyglycerol esters, sorbitan esters, fatty acid esters and/or dimethicone copolyols. Particularly preferred W/O emulsifiers are the sorbitol esters.

Preference is giving to using sorbitol esters obtainable by transesterifying sorbitol, optionally alkoxylated sorbitol, with fatty acid methyl esters or fatty acid triglycerides, the reaction products obtained by transesterification then optionally being alkoxylated. In the case of alkoxylated sorbitol as reaction product, this is preferably ethoxylated sorbitol. The content of ethoxylate groups is preferably 1 to 90 —$CH_2CH_2O$— groups per molecule of sorbitol. The alkoxylation of the sorbitol can be carried out by processes known to the person skilled in the art.

However, during the transesterification of sorbitol with fatty acid methyl esters, the procedure preferably involves firstly carrying out the transesterification with sorbitol and then alkoxylating the reaction product by known processes. The fatty acid radicals of fatty acid methyl esters and fatty acid triglycerides are preferably ($C_8$–$C_{22}$) radicals which are straight-chain and/or branched and saturated and/or unsaturated. Examples thereof are palmitic acid, stearic acid, lauric acid, linoleic acid, linolenic acid, isostearic acid or oleic acid. Examples of suitable fatty acid triglycerides are native animal or vegetable oils, fats and waxes, such as, for example, rapeseed oil, olive oil, palm kernel oil, sunflower oil, coconut oil, linseed oil, castor oil, soybean oil, optionally also in refined or hydrogenated form. Since the natural fats, oils and waxes normally comprise mixtures of fatty acid radicals of varying chain length, this applies correspondingly also to the sorbitol esters prepared therefrom.

For cosmetic and pharmaceutical applications, sorbitol esters based on rapeseed oil are particularly suitable.

The preparation of the sorbitol esters from fatty acid methyl esters or fatty acid triglycerides can be carried out according to DE 197 27 950 and EP-A-1029586.

The reaction of sorbitol with the fatty acid triglycerides or methyl esters is preferably carried out in a one-pot process without solvents at temperatures of, preferably, 120–140° C. in the presence of an alkaline catalyst. The molar ratio of sorbitol to fatty acid methyl ester is preferably 1:1 to 1:2. If fatty acid triglycerides are used, the molar ratio of sorbitol to fatty acid triglyceride is 1:3.5 to 1:4.5. The reaction time is preferably 12 to 13 hours.

If fatty acid methyl esters are used, the methanol which forms during the reaction is distilled off. Since sorbitol is usually commercially available as an aqueous solution, the water is advantageously removed prior to use by distillation at a maximum 120° C. under reduced pressure.

As well as containing residual amounts of unreacted sorbitol, the reaction product of this transesterification reaction essentially consists of the sorbitol monofatty acid esters and the sorbitol difatty acid esters. The corresponding triesters are formed only in minor amounts. If fatty acid triglycerides are used as starting material, the reaction product also comprises mono- and difatty acid glyceride and unreacted triglyceride, depending on the molar ratio of the starting compounds chosen in each case.

The hydrophobic/hydrophilic properties of the fine emulsion can be controlled through the choice of fatty acid component, where appropriate through the degree of ethoxylation and/or through the addition of neutralizing agent, but, in particular, through the choice of the hydrophilic component.

Suitable hydrophilic components are, preferably, surfactants, coemulsifiers, soil release polymers and/or acid/alkali components.

The surfactants used as hydrophilic components are anionic, cationic, zwitterionic, amphoteric and/or nonionic surfactants. Preference is given to using amphoteric surfactants.

Suitable anionic surfactants are, for example, $(C_{10}-C_{20})$-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkane sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkyl glyceride ether sulfonates, fatty acid methyltaurides, fatty acid sarcosinates, sulforicinoleates, amphoacetates or -glycinates and/or acyl glutamates. Said compounds or mixtures thereof are preferably used in the form of their water-soluble or water-dispersible salts, for example the sodium, potassium, magnesium, ammonium, mono-, di- and triethanolammonium and analogous alkylammonium salts.

Suitable cationic surfactants are, for example, quaternary ammonium salts, such as di-$((C_{10}-C_{24})$-alkyl) dimethylammonium chloride and bromide, preferably di-$((C_{12}-C_{18})$-alkyl)dimethylammonium chloride and bromide, $((C_{10}-C_{24})$-alkyl)dimethylethylammonium chloride and bromide; $((C_{10}-C_{24})$-alkyl)trimethylammonium chloride and bromide, preferably cetyltrimethylammonium chloride or bromide and $((C_{20}-C_{22})$-alkyl) trimethylammonium chloride and bromide; $((C_{10}-C_{24})$-alkyl)dimethylbenzylammonium chloride and bromide, preferably $((C_{12}-C_{18})$-alkyl)dimethylbenzylammonium chloride; N-$((C_{10}-C_{18})$-alkyl)pyridinium chloride and bromide, preferably N-$((C_{12}-C_{16})$-alkyl)pyridinium chloride and bromide; N-$((C_{10}-C_{18})$-alkyl)isoquinolinium chloride, bromide and monoalkyl sulfate; N-$((C_{12}-C_{18})$-alkyl)polyoylaminoformylmethylpyridinium chloride; N-$((C_{12}-C_{18})$-alkyl)-N-methylmorpholinium chloride, bromide and monoalkyl sulfate; N-$((C_{12}-C_{18}$-alkyl)-N-ethylmorpholinium chloride, bromide and monoalkyl sulfate; $((C_{16}-C_{18})$-alkyl)pentaoxethylammonium chloride; diisobutylphenoxyethoxyethyldimethylbenzylammonium chloride; salts of N,N-diethylaminoethylstearylamide and -oleylamide with hydrochloric acid, acetic acid, lactic acid, citric acid, phosphoric acid; N-acylaminoethyl-N,N-diethyl-N-methylammonium chloride, bromide and monoalkyl sulfate; and/or N-acylaminoethyl-N,N-diethyl-N-benzylammonium chloride, bromide or monoalkyl sulfate, where acyl is preferably stearyl or oleyl.

Suitable amphoteric surfactants are, preferably, N-$((C_{12}-C_{18})$-alkyl)-β-amino-propionates and N-$((C_{12}-C_{18})$-alkyl)-β-iminodipropionates as alkali metal and mono-, di- and trialkylammonium salts; N-acylaminoalkyl-N,N-dimethylacetobetaine, preferably N-$(C_8-C_{18}$-acyl)aminopropyl-N,N-dimethylacetobetaine; $((C_{12}-C_{18})$-alkyl)-dimethylsulfopropylbetaine; amphoteric surfactants based on imidazoline (Miranol®, Steinapon®), preferably the sodium salt of 1-(β-carboxymethyloxyethyl)-1-(carboxy-methyl)-2-laurylimidazolinium; and/or acylglutamates.

Particularly preferably suitable are the acylglutamates.

Suitable nonionic surfactants are, for example, fatty alcohol ethoxylates (alkyl polyethylene glycols); alkylphenol polyethylene glycols; alkyl mercaptan poly-ethylene glycol; fatty amine ethoxylates (alkylamino polyethylene glycols); fatty acid ethoxylates (acyl polyethylene glycols); polypropylene glycol ethoxylates (poloxamers); fatty acid amide polyethylene glycols; N-alkyl- and N-alkoxy-polyhydroxy fatty acid amides, in particular fatty acid N-methylglucamides; sucrose esters; polyglycol ethers; alkylpolyglycosides; phosphoric esters (mono-, di- and triphosphoric esters ethoxylated and nonethoxylated); and/or amine oxides, such as, for example, $((C_{12}-C_{18})$-alkyl) dimethylamine oxide and fatty acid amidoalkyldimethylamine oxide.

Suitable nonionogenic coemulsifiers are addition products of from 2 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group; $(C_{12}-C_{18})$-fatty mono- and diesters of addition products of from 1 to 30 mol of ethylene oxide with glycerol; glycerol mono- and diesters and sorbitan mono- and diesters of saturated and unsaturated fatty acids having 6 to 22 carbon atoms and ethylene oxide addition products thereof; addition products of from 15 to 60 mol of ethylene oxide with castor oil and/or hydrogenated castor oil; and/or polyol and, in particular, polyglycerol esters, such as, for example, polyglycerol polyricinoleate and polyglycerol poly-12-hydroxystearate.

The addition products of ethylene oxide and/or propylene oxide with fatty alcohols; fatty acids, alkylphenols; glycerol mono- and diesters; sorbitan mono- and diesters of fatty acids; and castor oil are known commercially available products. These are homolog mixtures whose average degree of alkoxylation corresponds to the ratio of the quantitative amounts of ethylene oxide and/or propylene oxide and substrate with which the addition reaction is carried out.

Likewise suitable as hydrophilic component are the polymers referred to as soil release polymers. Preferably suitable are oligoesters obtained by polycondensation of from 40 to 52 mol %, preferably 45 to 50 mol %, of one or more dicarboxylic acids and/or esters thereof; 10 to 40 mol %, preferably 20 to 35 mol %, of ethylene glycol and/or propylene glycol; 3 to 20 mol %, preferably 10 to 15 mol %, of polyethylene glycol; 0 to 10 mol % of a water-soluble addition product of from 5 to 80 mol of an alkylene oxide with 1 mol of ($C_1$–$C_{24}$)-alcohols, ($C_6$–$C_{18}$)-alkylphenols or ($C_8$–$C_{24}$)-alkylamines; and 0 to 10 mol % of one or more polyols having 3 to 6 hydroxyl groups.

In the case of the acid/alkali component, the hydrophilic component consists of an acid subcomponent and an alkali subcomponent. The W/O preemulsion is converted into the O/W fine emulsion by adding the acid subcomponent and then neutralizing the acid subcomponent by adding the alkali subcomponent. Preferred acids and alkalis are ether carboxylic acids and salts thereof or phosphoric mono- and/or diesters and neutralized salts thereof.

Suitable oily substances for the fine emulsions are, preferably, Guerbet alcohols having 6 to 18, preferably 8 to 10, carbon atoms; esters of linear ($C_6$–$C_{13}$)-fatty acids with linear ($C_6$–$C_{20}$)-fatty alcohols; esters of branched ($C_6$–$C_{13}$)-carboxylic acids having linear ($C_6$–$C_{20}$)-fatty alcohols, esters of linear ($C_6$–$C_{18}$)-fatty acids with branched alcohols, in particular 2-ethylhexanol; esters of linear and/or branched fatty acids with polyhydric alcohols (such as, for example, dimerdiol or trimerdiol) and/or Guerbet alcohols; triglycerides based on ($C_6$–$C_{10}$)-fatty acids; vegetable oils; branched primary alcohols; substituted cyclohexanes; Guerbet carbonates; dialkyl ethers; and/or aliphatic or aromatic hydrocarbons.

As auxiliaries and additives, the fine emulsions may comprise, for example, superfatting agents; fats; waxes; stabilizers; biogenic active ingredients; light protection substances (UV light protection filters, pigments, micropigments), antioxidants; hydrotropic agents; solubilizers; bodying agents; cationic polymers; glycerol; preservatives; dispersants; protein derivatives, such as, for example, gelatins, collagen hydrolysates, natural- and synthetic-based polypeptides, egg yolk; lecithin; lanolin and lanolin derivatives; fatty alcohols; silicones; deodorizing agents; substances with keratolytic and keratoplastic action; enzymes; carrier substances; moisture-donating substances; antimicrobially active agents; and/or dyes and fragrances.

Suitable superfatting agents are, for example, polyethoxylated lanolin derivatives; lecithin derivatives, polyol fatty acid esters, monoglycerides and fatty acid alkanolamides, the latter also serving as foam stabilizers. Typical examples of fats are glycerides. Suitable waxes are, inter alia, beeswax, paraffin wax or microcrystalline waxes, optionally in combination with hydrophilic waxes, such as, for example, cetylstearyl alcohol.

Suitable UV filters are, for example, 4-aminobenzoic acid; 3-(4'-trimethylammonium)benzylidene-bornan-2-one methylsulfate; 3,3,5-trimethylcyclohexyl salicylate; 2-hydroxy-4-methoxybenzophenone; 2-phenylbenzimidazole-5-sulfonic acid and its potassium, sodium and triethanolamine salts; 3,3'-(1,4-phenylenedimethine)bis(7,7-dimethyl-2-oxo-bicyclo[2.2.1] heptane-1-methanesulfonic acid and its salts; 1-(4-tert-butylphenyl)-3-(4-methoxyphenyl)propane-1,3-dione, 3-(4'-sulfo)benzylidenebornan-2-one and its salts; 2-ethylhexyl 2-cyano-3,3-diphenylacrylate; polymers of N-[2(and 4)-(2-oxo-born-3-ylidenemethyl)benzyl]acrylamide; 2-ethylhexyl 4-methoxycinnamate; ethoxylated ethyl 4-aminobenzoate; isoamyl 4-methoxycinnamate; 2,4,6-tris[p-(2-ethylhexyloxycarbonyl)anilino]-1,3,5-triazine; 2-(2H-benzotriazol-2-yl)-4-methyl-6-(2-methyl-3-(1,3,3,3-tetramethyl-1-(trimethyl-silyloxy)disiloxanyl)propyl) phenol; 4,4'-[(6-[4-((1,1-dimethylethyl)aminocarbonyl) phenylamino]-1,3,5-triazine-2,4-yl)-diimino]bis(benzoic 2-ethylhexyl ester); 3-(4'-methylbenzylidene)-D,L-camphor; 3-benzylidenecamphor; 2-ethylhexyl salicylate; 2-ethylhexyl 4-dimethylaminobenzoate; hydroxy-4-methoxybenzo-phenone-5-sulfonic acid (sulisobenzone) and the sodium salt; and/or 4-isopropylbenzyl salicylate.

Pigments/micropigments which may be used are, for example, microfine titanium dioxide and zinc oxide.

Suitable antioxidants are, for example, superoxide dismutase, tocopherol (vitamin E) and ascorbic acid (vitamin C).

Stabilizers which may be used are metal salts of fatty acids, such as, for example, magnesium, aluminum and/or zinc stearate. Biogenic active ingredients are to be understood as meaning, for example, plant extracts and vitamin complexes.

Suitable preservatives are, for example, phenoxyethanol, formaldehyde solution, parabens, pentanediol or sorbic acid.

Dyes which can be used are the substances approved and suitable for cosmetic purposes.

Particularly suitable thickeners and dispersants are ethylene glycol esters of fatty acids having 14 to 22, particularly preferably 16 to 22, carbon atoms, in particular mono- and diethylene glycol stearate. Also preferably suitable are stearin monoethanolamide, stearin diethanolamide, stearin isopropanolamide, stearin monoethanolamide stearate, stearyl stearate, cetyl palmitate, glyceryl stearate, stearamide diethanolamide distearate, stearamide monoethanolamide stearate, N,N-dihydrocarbyl-($C_{12}$–$C_{22}$)-amidobenzoic acid and soluble salts thereof, N,N-dihydrocarbyl-($C_{16}$–$C_{18}$)-amidobenzoic acid and soluble salts thereof and N,N-di ($C_{16}$–$C_{18}$)-amidobenzoic acid and derivatives thereof. Also particularly suitable are polyacrylates and carbomers, in particular those of water-soluble or water-swellable copolymers based on acrylamidoalkylsulfonic acids and N-vinylcarboxamides.

Suitable solubilizers are, in principle, all mono- and polyhydric alcohols and ethoxylated alcohols. Preference is given to using alcohols having 1 to 4 carbon atoms, such as, for example, ethanol, propanol, isopropanol, n-butanol and iso-butanol, glycerol and mixtures thereof. Also preferred are polyethylene glycols with a relative molecular mass below 2000. Particular preference is given to polyethylene glycols with a relative molecular mass between 200 and 600 in amounts up to 45% by weight and polyethylene glycols with a relative molecular mass between 400 and 600 in amounts of from 0.5 to 15% by weight. Further suitable solvents are, for example, triacetin(glycerol triacetate) and 1-methoxy-2-propanol.

Suitable carrier materials are, for example, vegetable oils, natural and hydrogenated oils, waxes, fats, water, alcohols, polyols, glycerol, glycerides, liquid paraffins, liquid fatty alcohols, sterols, polyethylene glycols, cellulose and cellulose derivatives.

Suitable fungicidal active ingredients are, preferably, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrethion and octopyrox.

Deodorizing substances which can be used are, for example, allantoin and bisabolol in amounts by weight of from 0.0001% to 10%.

Suitable cationic polymers are, for example, cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as, for example, amido-methicones; copolymers of adipic acid and dimethylaminohydroxypropyl-diethylenetriamine; polyaminopolyamide and cationic chitin derivatives, such as, for example, chitosan.

Suitable silicone compounds are, for example, dimethylpolysiloxane, methylphenylpolysiloxane, cyclic silicones and amino-, fatty-acid-, alcohol-, polyether-, epoxy-, fluorine- and/or alkyl-modified silicone compounds, and polyalkylsiloxanes, polyalkylarylsiloxanes, polyethersiloxane copolymers, as described in U.S. Pat No. 5,104,645 and the publications cited therein, which may be liquid or in the form of a resin at room temperature.

The compositions according to the invention can be mixed with conventional ceramides, pseudoceramides, fatty acid N-alkylpolyhydroxyalkylamides, cholesterol, cholesterol fatty acid esters, fatty acids, triglycerides, cerebrosides, phospholipids and similar substances.

Moisture-donating substances which are available are, for example, isopropyl palmitate, glycerol and/or sorbitol, which can be used in the quantitative amounts 0.1 to 50%.

The total fraction of auxiliaries and additives is, based on the finished fine emulsions, preferably 1 to 10% by weight, particularly preferably 2 to 5% by weight.

With regard to the problem of ethoxylated products discussed at the outset, the fine emulsions according to the invention are advantageously free from ethoxylated components (W/O emulsifiers, hydrophilic components etc.).

The fine emulsions according to the invention are preferably cosmetic and pharmaceutical spray emulsions, e.g. those for skincare. Examples which may be mentioned are body lotions, aftersun lotions, sunscreen compositions, lotions comprising pharmaceutically active ingredients, deodorant sprays and lotions for the preparation of moisture-impregnated cleansing and care wipes.

The invention also provides a process for the preparation of fine emulsions, which comprises converting a W/O preemulsion comprising at least one W/O emulsifier into an O/W fine emulsion by adding at least one hydrophilic component and, where appropriate, changing the temperature.

The particle size of the fine emulsions is preferably in the range 0.1 to 10 micrometers.

The W/O preemulsion is preferably converted into the O/W fine emulsion without increasing the temperature.

The amount of W/O emulsifiers which the W/O preemulsion comprises is measured such that the finished O/W fine emulsion preferably comprises 0.01 to 10% by weight, particularly preferably 0.1 to 8% by weight and especially preferably 0.2 to 4% by weight, of W/O emulsifiers.

The amount of hydrophilic components which are added to the W/O preemulsion is measured such that the finished O/W fine emulsion preferably comprises 0.01 to 10% by weight, particularly preferably 0.1 to 7% by weight and especially preferably 0.3 to 5% by weight, of hydrophilic components.

The nonaqueous fraction of the fine emulsions, which is largely composed of the W/O emulsifiers and the oily substance, is preferably 0.1 to 95% and particularly preferably 0.5 to 45% by weight.

The W/O emulsifiers are preferably sorbitol esters, polyglycerol esters, sorbitan esters, fatty acid esters and/or dimethicone copolyols.

As W/O emulsifiers, particular preference is given to the sorbitol esters described above.

Preference is given especially to sorbitol esters based on rapeseed oil.

The hydrophilic components are preferably the surfactants, coemulsifiers, soil release polymers and/or acid/alkali components described above. Preference is given to amphoteric surfactants, in particular acylglutamates.

In the case of the acid/alkali component, the process is notable for the fact that the hydrophilic component consists of an acid subcomponent and an alkali subcomponent. The W/O preemulsion is converted into the O/W fine emulsion by adding the acid subcomponent and then neutralizing the acid subcomponent by adding the alkali subcomponent.

Where appropriate, the additives and auxiliaries described above are added to the W/O preemulsion and/or the O/W fine emulsion. The weight fraction of additives and auxiliaries is preferably, based on the finished fine emulsion, 0.1 to 10% by weight.

Advantageously, no ethoxylated components (W/O emulsifiers, hydrophilic components etc.) are added to the fine emulsions during the preparation. The examples below serve to illustrate the invention but without limiting it. The percentages are percentages by weight.

EXAMPLES

Example 1

Sprayable Care O/W Microemulsion (No Ethoxylated Components)

| | |
|---|---|
| Emulsogen ® SRO (Clariant GmbH) (rapeseed oil sorbitol ester) | 4.0% |
| Soybean oil | 2.0% |
| Almond oil | 0.8% |
| Avocado oil | 0.8% |
| Jojoba oil | 0.4% |
| Cutina ® GMS (Cognis GmbH) Glyceryl stearate | 1.0% |
| Carbopol ® 980 (BF Goodrich) (Carbomer) | 0.2% |
| Water | 44.7% |
| Sodium hydroxide (10% aqueous solution) | 0.8% |
| Water | 44.9% |
| Hostapon ® CLG (Clariant GmbH) (Sodium lauroyl glutamate) | 0.6% |

Preparation
1) Heat emulsifier and oils to about 80° C.
2) Add carbomer

3) Heat 1$^{st}$ part of water with sodium hydroxide solution to about 80° C.
4) Add 1$^{st}$ part of water to the oil phase with stirring using dispersion equipment and disperse for about 2 minutes to give a W/O emulsion
5) Mix 2$^{nd}$ part of water with the acyl glutamate and add while cold with stirring, and after-stir for about 2 hours.

Example 2
Sprayable Care Emulsion (No Ethoxylated Components, can be Prepared in the Cold)

| | |
|---|---|
| Emulsogen ® SRO (Clariant GmbH) | 4.0% |
| (Rapeseed oil sorbitol ester) | |
| Soybean oil | 2.0% |
| Almond oil | 0.8% |
| Avocado oil | 0.8% |
| Jojoba oil | 0.4% |
| Isopropyl palmitate | 1.0% |
| Carbopol ® 980 (BF Goodrich) | 0.2% |
| (Carbomer) | |
| Water | 44.7% |
| Sodium hydroxide | 0.8% |
| (10% aqueous solution) | |
| Water | 44.9% |
| Hostapon ® CLG (Clariant GmbH) | 0.6% |
| (Sodium lauroyl glutamate) | |

Preparation
1) Mix emulsifier, oils and carbomer
2) Add 1$^{st}$ part of water with sodium hydroxide solution at room temperature to the oil phase with stirring using dispersion equipment and disperse for about 2 minutes to give a W/O emulsion
3) Mix 2$^{nd}$ part of water with the acyl glutamate and add while cold with stirring, then after-stir for about 2 hours.

Example 3
Sprayable Aftersun Emulsion

| | |
|---|---|
| Emulsogen ® SRO (Clariant GmbH) | 4.0% |
| (Rapeseed oil sorbitol ester) | |
| Soybean oil | 0.5% |
| Almond oil | 0.2% |
| Avocado oil | 0.2% |
| Jojoba oil | 0.1% |
| Emulsogen ® HCO 040 (Clariant GmbH) | 2.0% |
| (PEG-40 hydrogenated castor oil) | |
| Myritol ® 318 | 1.0% |
| (Caprylic/Capric triglyceride) | |
| Cetiol ® SN (Cognis GmbH) | 1.0% |
| (Cetearyl isononanoate) | |
| Mineral oil, low-viscosity | 1.0% |
| Cutina ® GMS (Cognis GmbH) | 0.2% |
| (Glyceryl stearate) | |
| Isopropyl palmitate | 1.0% |
| Lanette ® O (Cognis GmbH) | 0.2% |
| (Cetearyl alcohol) | |
| Carbopol ® 980 (BF Goodrich) | 0.2% |
| (Carbomer) | |
| Water | 38.0% |
| Sodium hydroxide | 0.7% |
| (10% aqueous solution) | |
| Water | 39.4% |
| Hostapon ® CLG (Clariant GmbH) | 0.6% |
| (Sodium lauroyl glutamate) | |
| Glycerol | 5.0% |
| Panthenol | 0.5% |
| Tocopheryl acetate | 0.2% |
| Ethanol | 4.0% |

Preparation
1) Heat emulsifier and oils to about 80° C.
2) Add carbomer
3) Heat 1$^{st}$ part of water with sodium hydroxide solution to about 80° C.
4) Add 1$^{st}$ part of water to the oil phase with stirring using dispersion equipment and disperse for about 2 minutes to give a W/O emulsion
5) Mix 2$^{nd}$ part of water with the acyl glutamate and, with glycerol and panthenol, add while cold with stirring, and after-stir for about 2 hours
6) Add tocopheryl acetate and ethanol, after-stir for about 0.5 hours.

What is claimed is:

1. A process for the preparation of fine emulsions, which comprises converting a W/O preemulsion comprising at least one W/O emulsifier into an O/W fine emulsion by adding at least one hydrophilic component and, where appropriate, changing the temperature, wherein the at least one W/O emulsifier is a sorbitol ester.

2. The process as claimed in claim 1, wherein the W/O preemulsion is converted into the O/W fine emulsion without increasing the temperature.

3. The process as claimed in claim 1, wherein the O/W fine emulsion comprises 0.01 to 10% by weight of W/O emulsifier.

4. The process as claimed in claim 1, wherein the O/W fine emulsion comprises 0.01 to 10% by weight of the hydrophilic component.

5. The process as claimed in claim 1, further comprising adding additives and auxiliaries to the W/O preemulsion and/or the O/W fine emulsion.

6. The process as claimed in claim 1, wherein no ethoxylated components are used during the preparation of the fine emulsion.

7. The process as claimed in claim 1, wherein the hydrophilic component is selected from the group consisting of surfactants, coemulsifiers, soil release polymers, acid/alkali components, and mixtures thereof.

8. The process as claimed in claim 7, wherein the surfactants are amphoteric surfactants.

* * * * *